(12) United States Patent
Tachibana

(10) Patent No.: US 8,294,127 B2
(45) Date of Patent: Oct. 23, 2012

(54) CHARGED-PARTICLE BEAM IRRADIATION DEVICE, CHARGED-PARTICLE BEAM IRRADIATION METHOD, AND COMPUTER READABLE MEDIUM

(75) Inventor: Masanori Tachibana, Niihama (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 13/207,521

(22) Filed: Aug. 11, 2011

(65) Prior Publication Data

US 2012/0049091 A1 Mar. 1, 2012

(30) Foreign Application Priority Data

Aug. 26, 2010 (JP) ................................ 2010-189816

(51) Int. Cl.
*G21K 5/00* (2006.01)
(52) U.S. Cl. ...................... 250/492.3; 250/310; 250/311
(58) Field of Classification Search .................. 250/306, 250/307, 309–311, 492.1, 492.2, 492.21, 250/492.3
See application file for complete search history.

(56) References Cited

U.S. PATENT DOCUMENTS

| | | | | |
|---|---|---|---|---|
| 5,260,579 A * | 11/1993 | Yasuda et al. | .............. | 250/492.2 |
| 7,102,144 B2 * | 9/2006 | Matsuda et al. | ........... | 250/492.1 |
| 7,122,811 B2 * | 10/2006 | Matsuda et al. | ........... | 250/492.3 |
| 7,227,161 B2 * | 6/2007 | Matsuda et al. | ........... | 250/492.3 |
| 7,425,717 B2 * | 9/2008 | Matsuda et al. | ........... | 250/492.3 |
| 7,560,717 B2 * | 7/2009 | Matsuda et al. | ........... | 250/505.1 |

FOREIGN PATENT DOCUMENTS

JP 2000-354673 12/2000

\* cited by examiner

*Primary Examiner* — Bernard E Souw
(74) *Attorney, Agent, or Firm* — Squire Sanders (US) LLP

(57) ABSTRACT

A charged-particle beam irradiation device, which irradiates an object to be irradiated with a charged-particle beam, includes a scanning member that scans the object to be irradiated with the charged-particle beam; an irradiation amount setting unit that sets an irradiation amount of the charged-particle beam at a plurality of target scanning positions on a scanning line of the charged-particle beam with which the scanning member scans the object to be irradiated; and a scanning speed setting unit that sets a target scanning speed of the charged-particle beam at each of the target scanning positions on the basis of the irradiation amount set by the irradiation amount setting unit.

6 Claims, 6 Drawing Sheets

CHARGED-PARTICLE BEAM IRRADIATION DEVICE, CHARGED-PARTICLE BEAM IRRADIATION METHOD, AND COMPUTER READABLE MEDIUM

RELATED APPLICATION

Priority is claimed to Japanese Patent Application No. 2010-189816, filed Aug. 26, 2010, the entire content of which is incorporated herein by reference.

BACKGROUND

1. Technical Field

The present invention relates to a charged-particle beam irradiation device, a charged-particle beam irradiation method, and a charged-particle beam irradiation program.

2. Description of the Related Art

For some time, there has been known a charged-particle beam irradiation device that irradiates an object to be irradiated (for example, a tumor in the body of a patient) with a charged-particle beam such as a proton beam and performs treatment on the object to be irradiated. A technique, which modulates the intensity of a charged-particle beam in order to adjust the irradiation amount of the charged-particle beam with which an object to be irradiated is irradiated, has been known as technique relevant to this device.

SUMMARY

It is desired to provide a charged-particle beam irradiation device, a charged-particle beam irradiation method, and a charged-particle beam irradiation program that can control the irradiation amount of a charged-particle beam with high accuracy.

As the result of devoted research, the inventors found that the scanning speed of a charged-particle beam has an effect on the control of the irradiation amount of a charged-particle beam with high accuracy.

According to an embodiment of the present invention, there is provided a charged-particle beam irradiation device that irradiates an object to be irradiated with a charged-particle beam. The charged-particle beam irradiation device includes a scanning member that scans the object to be irradiated with the charged-particle beam, an irradiation amount setting unit that sets an irradiation amount of the charged-particle beam at a plurality of target scanning positions on a scanning line of the charged-particle beam with which the scanning member scans the object to be irradiated, and a scanning speed setting unit that sets a target scanning speed of the charged-particle beam at each of the target scanning positions on the basis of the irradiation amount set by the irradiation amount setting unit.

Likewise, according to another embodiment of the present invention, there is provided a charged-particle beam irradiation method that irradiates an object to be irradiated with a charged-particle beam. The charged-particle beam irradiation method includes an irradiation amount setting step of setting an irradiation amount of the charged-particle beam at a plurality of target scanning positions on a scanning line of the charged-particle beam with which a scanning member scans the object to be irradiated, and a scanning speed setting step of setting a target scanning speed of the charged-particle beam at each of the target scanning positions on the basis of the irradiation amount set in the irradiation amount setting step.

Likewise, according to still another embodiment of the present invention, there is provided a non-transitory computer readable program causing a computer to execute a process for irradiating an object with a charged-particle beam, the process including setting an irradiation amount of a charged-particle beam at a plurality of target scanning positions on a scanning line of the charged-particle beam with which a scanning member scans an object to be irradiated, and setting a target scanning speed of the charged-particle beam at each of the target scanning positions on the basis of the irradiation amount set by the irradiation amount setting.

DETAILED DESCRIPTION

Figure 1:
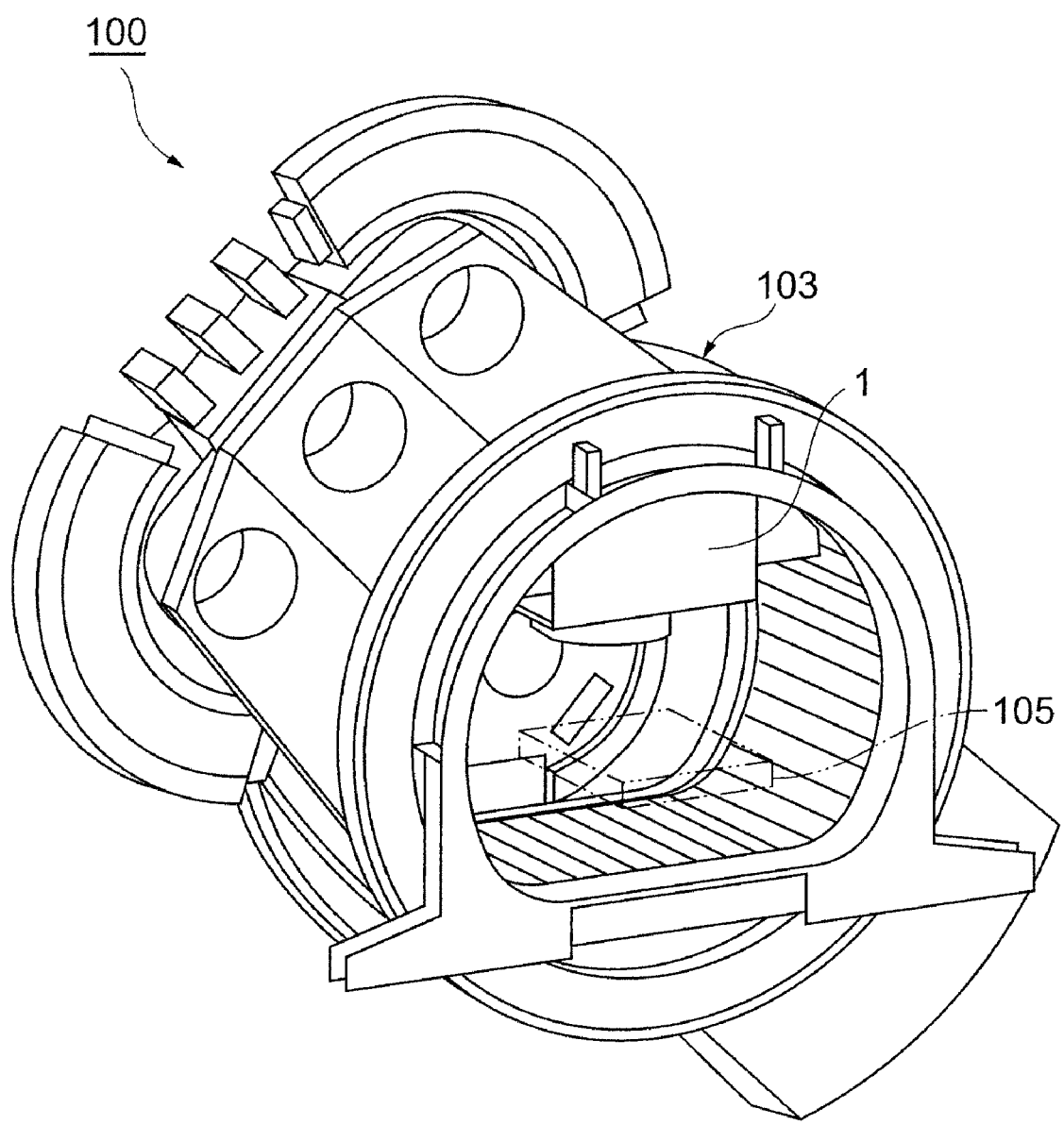
FIG. 1 is a perspective view of a charged-particle beam therapeutic apparatus to which a charged-particle beam irradiation device according to an embodiment of the invention is applied.

Here, since the intensity of a charged-particle beam is unstable, it is difficult to accurately modulate beam intensity. For this reason, in a method of adjusting the irradiation amount of a charged-particle beam while using beam intensity as a control amount, there is a problem in that it is not possible to control the irradiation amount with high accuracy.

Further, in a field where a charged-particle beam irradiation device is applied, it is preferable that the peripheral portion of an object to be irradiated not be irradiated with a charged-particle beam and that only the object to be irradiated be irradiated as in the radiation treatment of a tumor in the body of a patient. Accordingly, there is a demand for a device that can irradiate a desired object to be irradiated with a charged-particle beam with high accuracy.

According to the charged-particle beam irradiation device, the charged-particle beam irradiation method, and the charged-particle beam irradiation program, if the irradiation amount of the charged-particle beam is set at each of the plurality of target scanning positions of the charged-particle beam on the object to be irradiated, the target scanning speed of the charged-particle beam at each of the target scanning positions is set on the basis of this irradiation amount. Since the scanning speed of the charged-particle beam is easily stabilized as compared to beam intensity that has been used as a control amount of the irradiation amount of a charged-particle beam in the past, it is possible to accurately modulate the scanning speed to a desired value. Accordingly, if a target scanning speed is used as a control amount for adjusting the irradiation amount of the charged-particle beam, it is possible to accurately modulate a control amount to a desired value. As a result, it is possible to control the irradiation amount of the charged-particle beam with high accuracy.

Further, the charged-particle beam irradiation device may further include a control unit that controls the scanning member according to the target scanning position and the target scanning speed so that the object to be irradiated is scanned with the charged-particle beam.

Due to this structure, when the target scanning speed, which can be stably adjusted, is used as a control amount for adjusting the irradiation amount of the charged-particle beam, it is possible to accurately modulate the control amount to a desired value. As a result, it is possible to control the irradiation amount of the charged-particle beam with high accuracy.

Further, the charged-particle beam irradiation device may further include a measurer that measures a scanning position and a scanning speed of the charged-particle beam with which the scanning member scans the object to be irradiated. The control unit may control the scanning member by performing position/speed feedback control for adjusting a control input to the scanning member so that an error between the target scanning position and the scanning position measured by the measurer is eliminated and an error between the target scanning speed and the scanning speed measured by the measurer is eliminated.

Due to this structure, the control unit controls the scanning member by performing position/speed feedback control on the basis of the scanning position and the scanning speed of the charged-particle beam. Accordingly, the followability to a target scanning position and a target scanning speed is improved and it is possible to control the irradiation amount of the charged-particle beam with higher accuracy.

Further, the charged-particle beam irradiation device may further include a beam intensity detector that detects intensity of the charged-particle beam. The control unit may adjust the scanning speed of the scanning member so as to offset the change of beam intensity when the beam intensity detected by the beam intensity detector is changed to the outside of a predetermined error range.

According to this structure, even when the intensity of the charged-particle beam is changed, it is possible to continue the irradiation of the charged-particle beam at accurate irradiation amount.

According to the charged-particle beam irradiation device, the charged-particle beam irradiation method, and the charged-particle beam irradiation program of the embodiments of the invention, it is possible to control the irradiation amount of a charged-particle beam with high accuracy.

Preferred embodiments of the invention will be described in detail below with reference to the drawings. Meanwhile, the same or corresponding elements in the following description are denoted by the same reference numerals and repeated description will be omitted.

Figure 2:
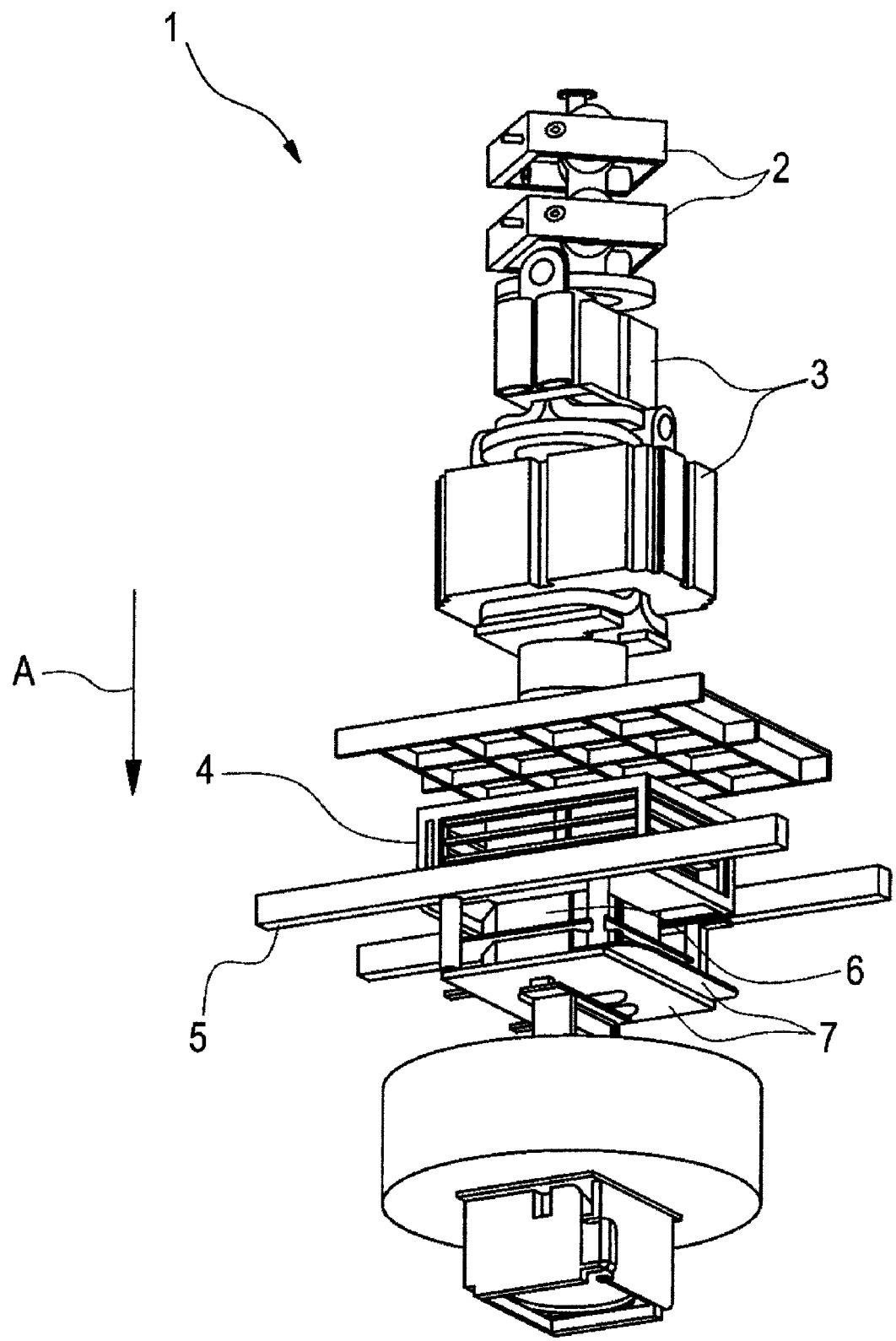
FIG. 2 is a perspective view of the charged-particle beam irradiation device shown in FIG. 1.
Figure 3:
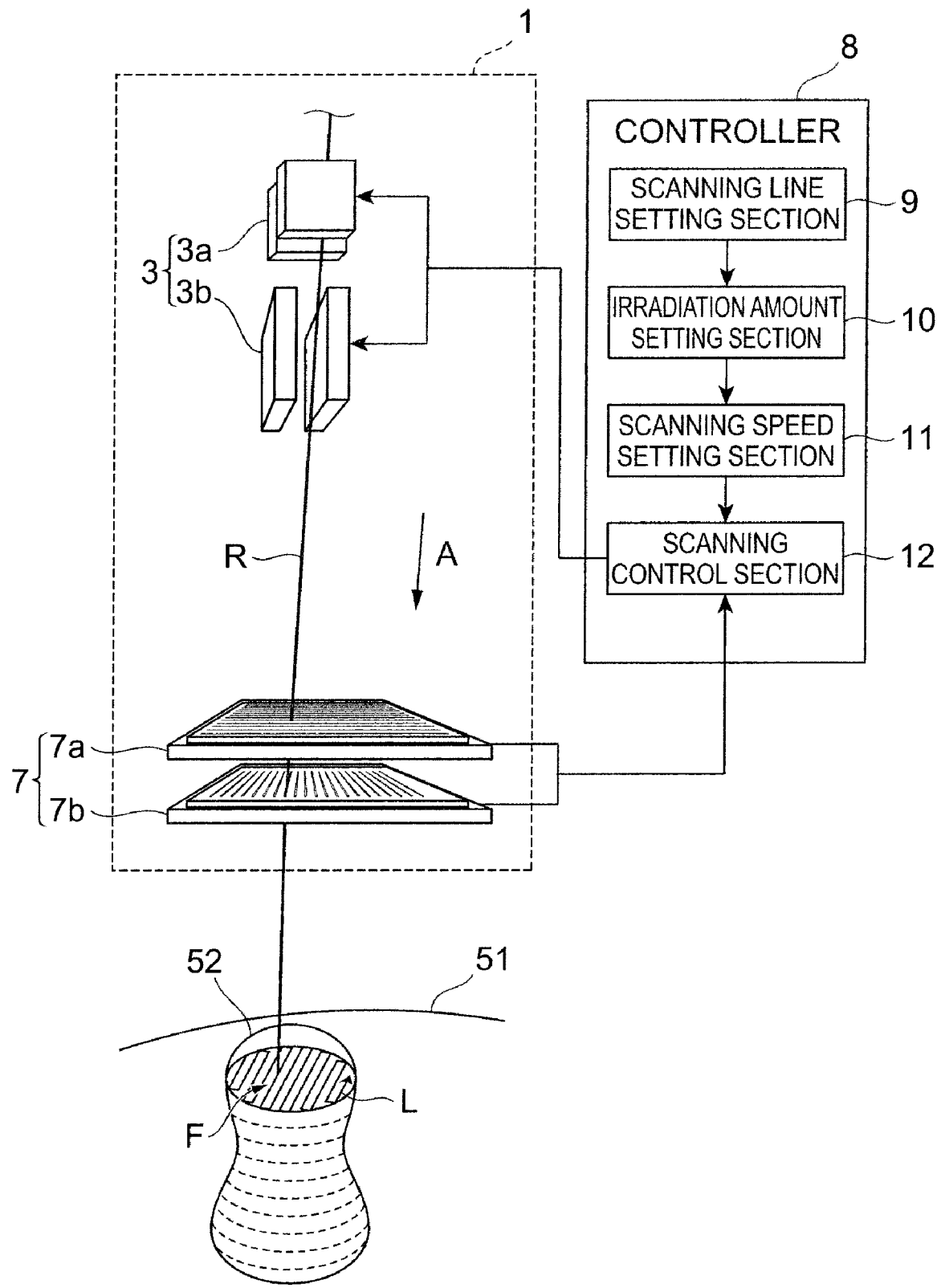
FIG. 3 is a view showing a control system of the charged-particle beam irradiation device.

FIG. 1 is a perspective view of a charged-particle beam therapeutic apparatus to which a charged-particle beam irradiation device according to an embodiment of the invention is applied, FIG. 2 is a perspective view of the charged-particle beam irradiation device shown in FIG. 1, and FIG. 3 is a view showing a control system of the charged-particle beam irradiation device.

As shown in FIG. 1, in a charged-particle beam irradiation device 100, an irradiation unit 1 is mounted on a rotating gantry 103 that is provided so as to surround a treatment table 105, and can be rotated around the treatment table 105 by the rotating gantry 103. Further, a tumor 52 (an object to be irradiated) in the body of a patient who lies on the treatment table 105 is irradiated with a charged-particle beam R in an irradiation direction A (see FIG. 3). Although not shown in FIG. 1, the charged-particle beam irradiation device 100 includes a cyclotron that generates a charged-particle beam R by accelerating charged particles and is disposed at a position distant from the treatment table 105 and the rotating gantry 103. The cyclotron and the irradiation unit 1 are connected to each other by a beam transport system (beam transport line) that transmits a charged-particle beam R. Meanwhile, the cyclotron may not be provided at the position distant from the rotating gantry 103 and may be mounted on the rotating gantry 103. Further, instead of a cyclotron, the charged-particle beam irradiation device may use a synchrotron or a synchrocyclotron to generate a charged-particle beam R.

As shown in FIG. 3, the irradiation unit 1 continuously irradiates the tumor 52 in the body of a patient 51 lying on the treatment table 105 with a charged-particle beam R. Specifically, the irradiation unit 1 divides the tumor 52 into a plurality of layers in a depth direction (a Z-direction or the irradiation direction A), and performs continuous irradiation (so-called raster scanning or line scanning) while scanning the layer with a charged-particle beam R at a scanning speed V along a scanning line L in an irradiation field F that is set at each of the layers. That is, the irradiation unit 1 divides the tumor 52 into a plurality of layers and performs plane scanning on the respective layers in order to form a three-dimensional irradiation field corresponding to the tumor 52. Accordingly, the irradiation of a charged-particle beam R is performed so as to correspond to the three-dimensional shape of the tumor 52.

The charged-particle beam R is obtained by accelerating particles, which have charges, at high speed. A heavy particle (heavy ion) beam, an electron beam, and the like may be used as the charged-particle beam R. The irradiation field F is a region that has the maximum area of, for example, 200 mm×200 mm, and has a rectangular outer shape. Meanwhile, the shape of the irradiation field F may be various shapes, and may also be the shape corresponding to the shape of, for example, the tumor 52. The scanning line L is an expected line (imaginary line) along which the irradiation of the charged-particle beam R is be performed. The scanning line L of the above-mentioned rectangular irradiation field F extends in the shape of a rectangular wave in an example of line scanning. Meanwhile, the shape of the scanning line L is not limited to the shape of a rectangular wave, and may ea spiral shape or the like. In short, as long as the irradiation field F is filled, the shape of the scanning line L may be any shape.

As shown in FIG. 2, the irradiation unit 1 includes quadrupole magnets 2, a scanning magnet (scanning member) 3, a dose monitor (beam intensity detector) 4, an X-ray tube 5, a flat monitor (flatness monitor) 6, and a beam position monitor (measurer) 7. The quadrupole magnets 2 are sequentially arranged in the irradiation direction A of the charged-particle beam R, suppress the diffusion of the charged-particle beam R input from the cyclotron through the beam transport line, and cause the charged-particle beam to converge. The scanning magnet 3 scans a tumor in an X-direction and a Y-direction with the charged-particle beam R. The dose monitor 4 measures the dose of the charged-particle beam R (beam intensity). The X-ray tube 5 irradiates the tumor with an X ray when a CT image is taken with an X ray to check the position, size, and shape of the tumor 52 before and after the irradiation of the charged-particle beam R. The flat monitor 6 measures the flatness of a beam (charged-particle beam) (the flatness in the depth where a beam reaches) in the irradiation field F. The beam position monitor 7 measures the positions of the charged-particle beam R in the X-direction and the Y-direction.

Meanwhile, as shown in FIG. 3, the X-direction and the Y-direction are two directions that are perpendicular to the Z-direction (irradiation direction A) and orthogonal to each other, and are two directions that specify the position on the plane formed by the irradiation field F of the tumor 52. Further, as shown in FIG. 3, the scanning magnet 3 includes a set of electromagnets 3a that controls the scanning position of the charged-particle beam R in the X-direction, and a set of electromagnets 3b that adjusts the scanning position of the charged-particle beam R in the Y-direction. The beam position monitor 7 includes a grid wire 7a that detects the scanning position of the charged-particle beam R in the X-direction and a grid wire 7b that detects the scanning position of the charged-particle beam in the Y-direction.

In particular, in this embodiment, the irradiation unit 1 is adjusted so as to adjust the irradiation amount of the charged-particle beam R on the basis of a scanning speed at each of the scanning positions of the scanning line L on the irradiation field F. Here, in this embodiment, "the irradiation amount" of the charged-particle beam R means the amount of charged particles with which the tumor 52 is irradiated.

A control system of the irradiation unit 1 will be described below with reference to FIG. 3. The beam position monitor 7 and the scanning magnet 3 of the irradiation unit 1, and a controller 8, which is disposed outside the irradiation unit 1 and is connected to the scanning magnet 3 and the beam position monitor 7 so as to be capable of communicating with the scanning magnet 3 and the beam position monitor 7, are shown in FIG. 3 as a control system of the irradiation unit 1.

The controller 8 determines the irradiation amount of the charged-particle beam at every target scanning position of the charged-particle beam R on the scanning line L in the irradiation field F, and determines a scanning track (target scanning positions and a target scanning speed) in order to realize the determined irradiation amount of the charged-particle beam. Further, the controller performs the position/speed feedback control of the scanning magnet 3 on the basis of the scanning track of the charged-particle beam R that is measured by the beam position monitor 7.

As shown in FIG. 3, the controller 8 includes a scanning line setting section 9, an irradiation amount setting section (irradiation amount setting unit) 10, a scanning speed setting section 11, and a scanning control section (control unit) 12.

The scanning line setting section 9 sets the scanning line L of the charged-particle beam R with which the scanning magnet 3 scans the tumor 52. In more detail, the scanning line setting section 9 sets a scanning line L according to the shape of the irradiation field F of the tumor 52 so that the entire irradiation field F is scanned with a charged-particle beam R. For example, if the irradiation field F has a rectangular shape, the scanning line L is formed in the shape of a rectangular wave. The scanning line setting section 9 sets a plurality of target scanning positions on the set scanning line L. The target scanning positions are used as target values of the position feedback control by a scanning control section 12 to be described below. For example, the target scanning positions are set on the scanning line L at regular intervals. The scanning line setting section 9 transmits the information about the target scanning positions to the irradiation amount setting section 10.

The irradiation amount setting section 10 determines the irradiation amount of the charged-particle beam R at each of the target scanning positions on the scanning line L that is set by the scanning line setting section 9. The irradiation amount of the charged-particle beam R may be acquired by an operator's input operation of the irradiation unit 1, and may be set with reference to a given database and the like according to conditions, such as the state of the tumor and the depth of the irradiation field F. The irradiation amount setting section 10 sets the irradiation amount of a charged-particle beam R at each of the target scanning positions, and transmits the information about the set irradiation amount to the scanning speed setting section 11.

The scanning speed setting section 11 sets the target scanning speed of the charged-particle beam R at each of the target scanning positions on the basis of the irradiation amount of the charged-particle beam that is set by the irradiation amount setting section 10. When the intensity of the charged-particle beam R is constant, there is a unique correspondence relationship between the scanning speed and irradiation amount of the charged-particle beam R. Accordingly, the scanning speed setting section 11 keeps a table where, for example, the irradiation amount and scanning speed of the charged-particle beam correspond to each other, selects a scanning speed corresponding to a given irradiation amount, and sets the scanning speed as a target scanning speed. Here, it is preferable that a target scanning speed be set low with the increase of the given irradiation amount and be set high with the decrease of the given irradiation amount. The scanning speed setting section 11 forms a target scanning track by making the set target scanning speed and the target scanning position correspond to each other, and transmits the target scanning track to the scanning control section 12.

The scanning control section 12 controls the scanning magnet 3 according to the target scanning track (the target scanning position and the target scanning speed) so that the tumor 52 is scanned with a charged-particle beam R. Specifically, the scanning control section 12 performs the position/speed feedback control of the current intensity transmitted to a power source (not shown), which generates current for adjusting a magnetic force of the scanning magnet 3, as a control input of the scanning magnet. In more detail, the scanning control section adjusts a control input to the scanning magnet 3 (current intensity of the power source) by performing position/speed feedback control so that an error between the target scanning position and the scanning position of an actual charged-particle beam R measured by the beam position monitor 7 is eliminated and an error between the target scanning speed and the scanning speed of an actual charged-particle beam R measured by the beam position monitor 7 is eliminated.

Figure 4:
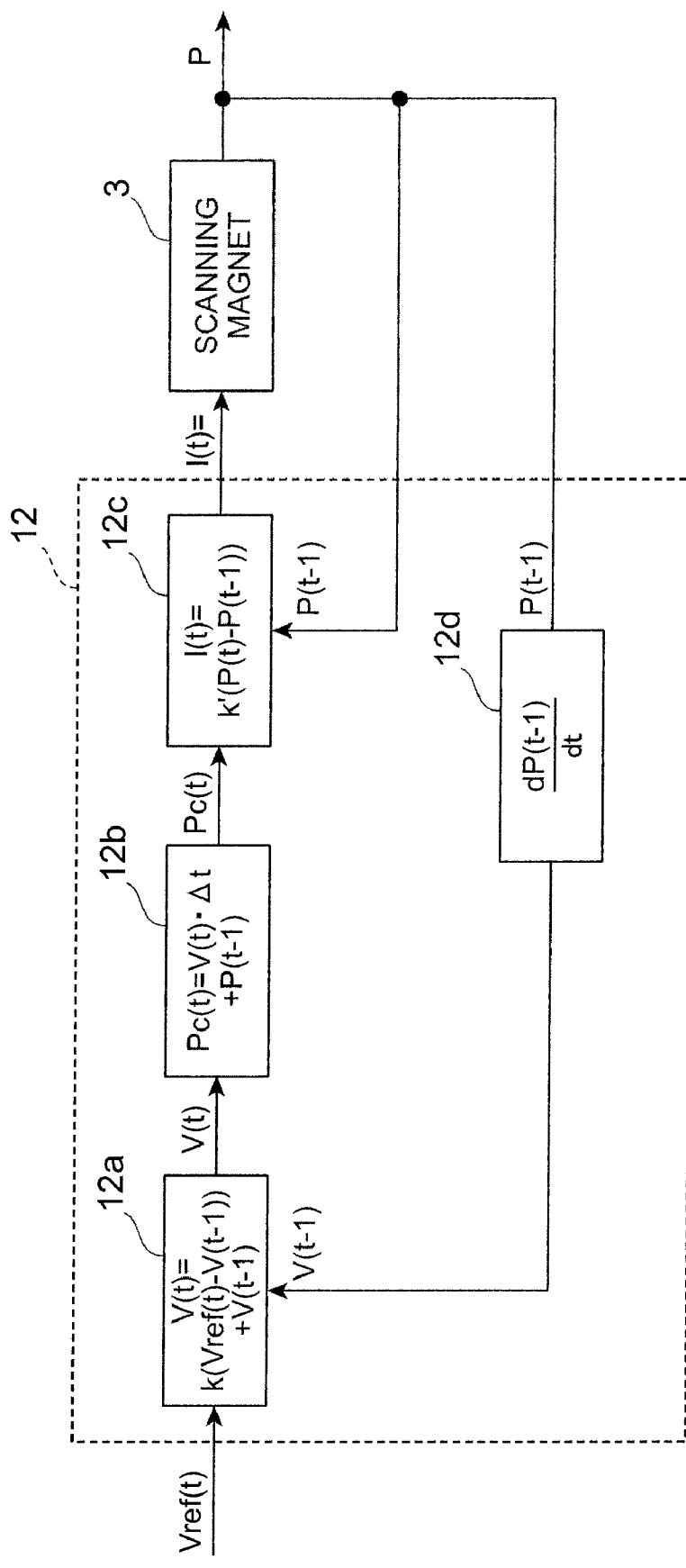
FIG. 4 is a block diagram illustrating position feedback control of a scanning control section.

The details of the position feedback control of the scanning control section 12 will be described here with reference to FIG. 4. FIG. 4 is a block diagram illustrating the position feedback control of the scanning control section 12. A region, which is surrounded by a broken line in FIG. 4, corresponds to the processing of the scanning control section 12.

First, as shown in a block 12a of FIG. 4, a scanning speed V(t) at a time t such as the following Expression (1) is obtained from the multiplication of a difference between a target scanning speed Vref(t) at a time t and a scanning speed V(t-1) at a time t-1 before one step, which is measured by the beam position monitor 7, and a constant k. Meanwhile, for example, as shown in a block 12d, it is possible to obtain the scanning speed V(t-1) from the first-order differentiation of a scanning position P(t-1) of a charged-particle beam R at a time t-1 before one step, which is measured by the beam position monitor 7, with respect to a time t.

$$V(t) = k \cdot (V\mathrm{ref}(t) - V(t-1)) + V(t-1) \tag{1}$$

Then, as shown in a block 12b of FIG. 4, a theoretical scanning position Pc(t) at a time t such as the following Expression (2) is obtained from the multiplication of a time width Δt (a difference between a time t and a time t-1) and the scanning speed V(t) obtained from Expression (1). Meanwhile, this Pc(t) is a value corresponding to a target scanning position Pref(t).

$$Pc(t)=V(t)\cdot\Delta t+P(t-1) \quad (2)$$

Next, as shown in a block 12c of FIG. 4, a control input I(t) to the scanning magnet 3 such as following Expression (3) is obtained from the multiplication of a difference between a theoretical scanning position Pc(t) obtained from Expression (2) and a scanning position P(t-1) at a time t-1 before one step, which is measured by the beam position monitor 7, and a constant k'. Specifically, this control input is the current intensity of a power source (not shown) that generates a magnetic force of the scanning magnet 3.

$$I(t)=k'\cdot(Pc(t)-P(t-1)) \quad (3)$$

When the current intensity of the power source of the scanning magnet 3 is adjusted on the basis of the current intensity obtained from Expression (3), the magnetic force of the scanning magnet 3 is adjusted according to the current intensity. As a result, the scanning position of a charged-particle beam R is adjusted. The scanning position P(t) at this time is measured by the beam position monitor 7, and is fed back to the block 12a and the block 12c.

Meanwhile, since the scanning magnet 3 and the beam position monitor 7 are adapted to individually perform control and measurement in the X-direction and the Y-direction, respectively, each of the scanning position P, the scanning speed V, the theoretical scanning position Pc, and the target scanning speed Vref is formed of a two-dimensional vector that includes an X-direction component and a Y-direction component.

The controller 8 is physically formed of a computer that includes a CPU (Central Processing Unit), a RAM (Random Access Memory) and a ROM (Read Only Memory) that are main storages, an auxiliary storage such as a hard disk, an input unit such as input keys that are an input device, an output unit such as a display, a communication module, and the like. The respective functions of the controller 8 shown in FIGS. 3 and 4 are realized by reading and writing data on the RAM or the ROM, and auxiliary storage device and operating the input unit, the output unit, and the communication module under the control of the CPU by making predetermined computer software be read in hardware such as a CPU, a RAM, and a ROM.

Figure 5:
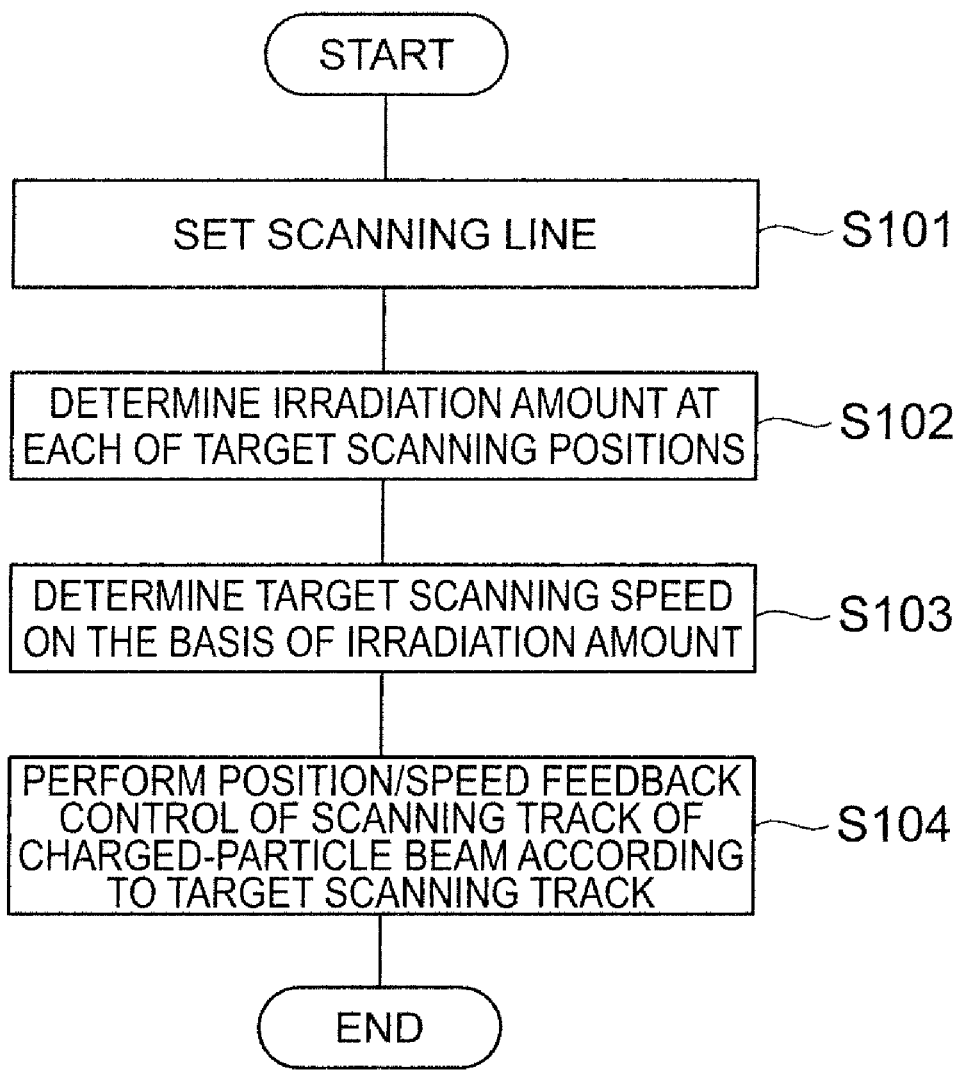
FIG. 5 is a flowchart illustrating processing that is performed in the charged-particle beam irradiation device according to an embodiment of the invention.

Next, with reference to FIG. 5, the processing performed in the irradiation unit 1 of this embodiment will be described and a charged-particle beam irradiation method according to this embodiment will be described.

First, the scanning line L of a charged-particle beam R with which the scanning magnet 3 scan the tumor 52 is set by the scanning line setting section 9 (S101). The scanning line setting section 9 sets a plurality of target scanning positions, which are used as target values of position feedback control, on the set scanning line L, and transmits the information about the target scanning positions to the irradiation amount setting section 10.

Then, the irradiation amount of the charged-particle beam R at each of the target scanning positions, which are set in Step S101, is set by the irradiation amount setting section 10 (S102: an irradiation amount setting step). The irradiation amount of the charged-particle beam R may be acquired by an operator's input operation of the irradiation unit 1, and may be set with reference to a given database and the like according to conditions, such as the state of the tumor and the depth of the irradiation field F. The irradiation amount setting section 10 sets the irradiation amount of a charged-particle beam R at each of the target scanning positions, and transmits the information about the set irradiation amount to the scanning speed setting section 11.

After that, the target scanning speed of the charged-particle beam R at each of the target scanning positions is set by the scanning speed setting section 11 on the basis of the irradiation amount of the charged-particle beam that is set in Step S102 (S103: scanning speed setting step). The scanning speed setting section 11 keeps a table where, for example, the irradiation amount and the scanning speed correspond to each other, selects a scanning speed corresponding to a given irradiation amount, and sets the scanning speed as a target scanning speed. The scanning speed setting section 11 forms a target scanning track by making the set target scanning speed and the target scanning position correspond to each other, and transmits the target scanning track to the scanning control section 12.

Further, the scanning magnet 3 is controlled by the scanning control section 12 according to the target scanning track (the target scanning position and the target scanning speed) so that the tumor 52 is scanned with a charged-particle beam R (S104). As described with reference to FIG. 4, the scanning control section 12 performs the position/speed feedback control of the scanning track of the charged-particle beam R by adjusting the current intensity of a power source, which adjusts the magnetic force of the scanning magnet 3, while using the target scanning track as a control input and using the scanning track (the scanning position and the scanning speed) of an actual charged-particle beam R, which is measured by the beam position monitor 7, as a feedback component.

Figure 6:
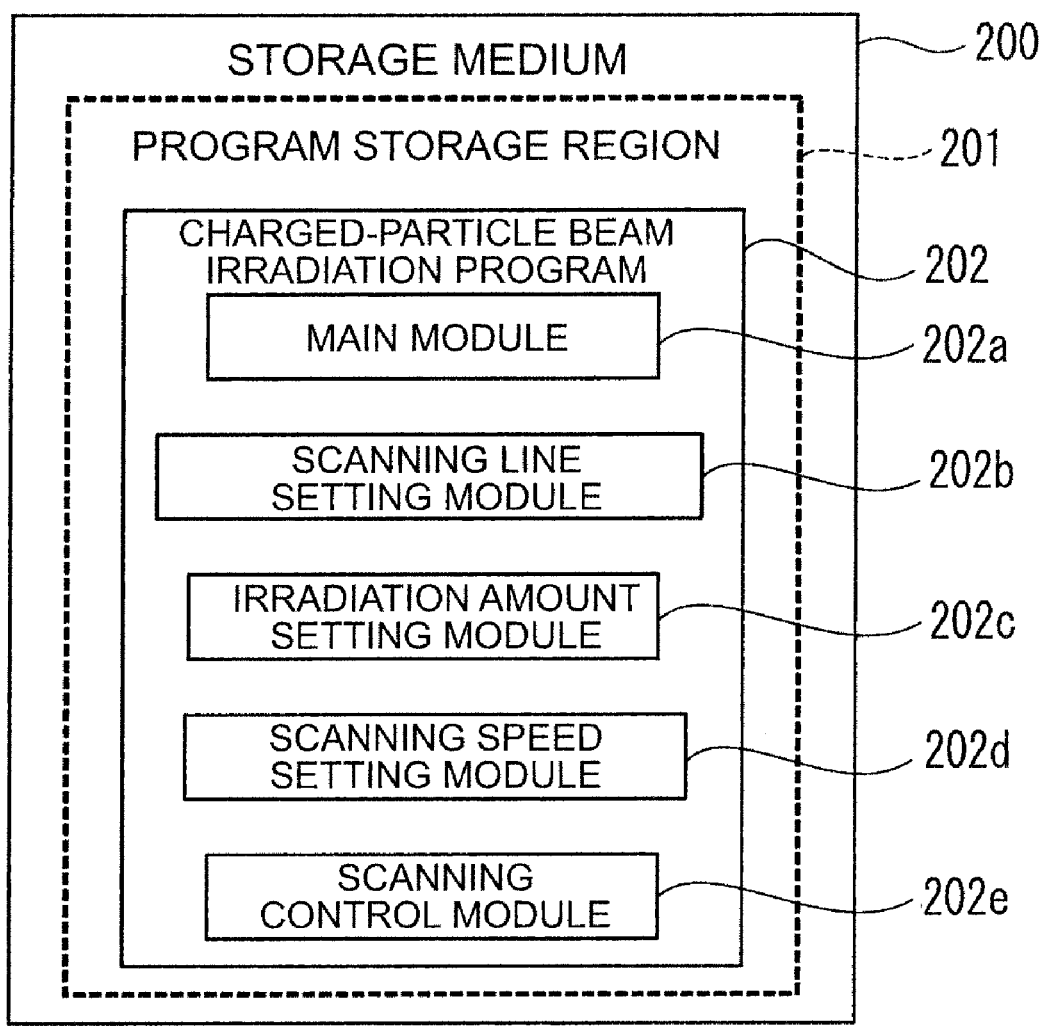
FIG. 6 is a view showing the configuration of a charged-particle beam irradiation program according to an embodiment of the invention.

Next, a charged-particle beam irradiation program for making a computer perform a series of processes, which is performed in the above-mentioned irradiation unit 1, will be described with reference to FIG. 6. As shown in FIG. 6, a charged-particle beam irradiation program 202 is stored in a program storage region 201 that is formed in a storage medium 200 of a computer.

The charged-particle beam irradiation program 202 includes a main module 202a that generally controls charged-particle beam irradiation processing, a scanning line setting module 202b, an irradiation amount setting module (an irradiation amount setting function) 202c, a scanning speed setting module (scanning speed setting function) 202d, and a scanning control module 202e.

Functions, which are realized by implementing the scanning line setting module 202b, the irradiation amount setting module 202c, the scanning speed setting module 202d, and the scanning control module 202e, are the same as the functions of the scanning line setting section 9, the irradiation amount setting section 10, the scanning speed setting section 11, and the scanning control section 12 of the above-mentioned controller 8 shown in FIG. 3, respectively.

Meanwhile, a part or all of the charged-particle beam irradiation program 202 may be adapted so as to be transmitted through a transmission medium such as a communication line, and received and recorded (including installation) by other devices. Further, a part or all of the charged-particle beam irradiation program 202 may be adapted so as to be recorded (including installation) in other devices from a state where a part or all of the charged-particle beam irradiation program is stored in portable storage media, such as a CD-ROM, a DVD-ROM, and a flash memory.

According to the charged-particle beam irradiation device, the charged-particle beam irradiation method, and the charged-particle beam irradiation program, if the irradiation amount of the charged-particle beam R is set at each of the target scanning positions of the charged-particle beam R on the tumor 52, the target scanning speed of the charged-particle beam R at each of the target scanning positions is set on the basis of this irradiation amount. Since the scanning speed of the charged-particle beam R is easily stabilized as compared to beam intensity that has been used as a control amount of the irradiation amount of a charged-particle beam R in the past, it is possible to accurately modulate the scanning speed to a desired value. Accordingly, if a target scanning speed is used as a control amount for adjusting the irradiation amount of the charged-particle beam R, it is possible to accurately modulate a control amount to a desired value. As a result, it is possible to control the irradiation amount of the charged-particle beam R with high accuracy.

Further, the scanning control section 12 controls the scanning magnet 3 according to the target scanning position and the target scanning speed so that the tumor 52 is scanned with a charged-particle beam R. Accordingly, when the target scanning speed, which can be stably adjusted, is used as a control amount for adjusting the irradiation amount of the charged-particle beam R, it is possible to accurately modulate the control amount to a desired value. As a result, it is possible to control the irradiation amount of the charged-particle beam R with high accuracy.

Furthermore, the scanning control section 12 controls the scanning magnet 3 by performing position/speed feedback control for adjusting a control input to the scanning magnet 3 (current intensity) so that an error between the target scanning position and the scanning position measured by the beam position monitor 7 is eliminated and an error between the target scanning speed and the scanning speed measured by the beam position monitor 7 is eliminated. For this reason, since the scanning control section controls the scanning magnet 3 by performing position/speed feedback control on the basis of the scanning position and the scanning speed of the charged-particle beam R, the followability to a target scanning position and a target scanning speed is improved and it is possible to control the irradiation amount of the charged-particle beam R with higher accuracy.

The charged-particle beam irradiation device, the charged-particle beam irradiation method, and the charged-particle beam irradiation program according to preferred embodiments of the invention have been described above. However, the invention is not limited to the above-mentioned embodiments. The position/speed feedback control performed by the scanning control section 12 may have a configuration different from the configuration of the block diagram shown in FIG. 4. For example, the power source of the scanning magnet 3 may be adjusted by individually performing position feedback control based on a target scanning position and speed feedback control based on a target scanning speed, and using a value, which is obtained by adding both control outputs, as current intensity.

Further, the scanning control section 12 monitors the intensity of a charged-particle beam R detected by the dose monitor 4, and a control for adjusting scanning speed by the scanning magnet 3 may be further performed so that a given irradiation amount is realized through the offset of change of beam intensity when the beam intensity is changed to the outside of a predetermined error range. That is, when the beam intensity, which should be constant, is changed so as to become a value not smaller than a predetermined upper limit, the scanning control section 12 increases the scanning speed. When the beam intensity becomes a value not larger than a predetermined lower limit, the scanning control section 12 decreases the scanning speed. Meanwhile, the upper and lower limits are set as upper and lower limits of an error range of allowable beam intensity. Even with consideration for the change of the intensity of the charged-particle beam R, it is possible to continue the irradiation of the charged-particle beam R at accurate irradiation amount by this control. Further, it is possible to avoid the interruption of treatment that is caused by the change of beam intensity.

It should be understood that the invention is not limited to the above-described embodiment, but may be modified into various forms on the basis of the spirit of the invention. Additionally, the modifications are included in the scope of the invention.

What is claimed is:

1. A charged-particle beam irradiation device that irradiates an object to be irradiated with a charged-particle beam, the charged-particle beam irradiation device comprising:
   a scanning member that scans the object to be irradiated with the charged-particle beam;
   an irradiation amount setting unit that sets an irradiation amount of the charged-particle beam at a plurality of target scanning positions on a scanning line of the charged-particle beam with which the scanning member scans the object to be irradiated; and
   a scanning speed setting unit that sets a target scanning speed of the charged-particle beam at each of the target scanning positions on the basis of the irradiation amount set by the irradiation amount setting unit.

2. The charged-particle beam irradiation device according to claim 1, further comprising:
   a control unit that controls the scanning member according to the target scanning position and the target scanning speed so that the object to be irradiated is scanned with the charged-particle beam.

3. The charged-particle beam irradiation device according to claim 2, further comprising:
   a measurer that measures a scanning position and a scanning speed of the charged-particle beam with which the scanning member scans the object to be irradiated,
   wherein the control unit controls the scanning member by performing position/speed feedback control for adjusting a control input to the scanning member so that an error between the target scanning position and the scanning position measured by the measurer is eliminated and an error between the target scanning speed and the scanning speed measured by the measurer is eliminated.

4. The charged-particle beam irradiation device according to claim 1, further comprising:
   a beam intensity detector that detects intensity of the charged-particle beam,
   wherein the control unit adjusts scanning speed of the scanning member so as to offset the change of beam intensity when the beam intensity detected by the beam intensity detector is changed to the outside of a predetermined error range.

5. A charged-particle beam irradiation method that irradiates an object to be irradiated with a charged-particle beam, the charged-particle beam irradiation method comprising:
   an irradiation amount setting step of setting an irradiation amount of the charged-particle beam at a plurality of target scanning positions on a scanning line of the charged-particle beam with which a scanning member scans the object to be irradiated; and
   a scanning speed setting step of setting a target scanning speed of the charged-particle beam at each of the target scanning positions on the basis of the irradiation amount set in the irradiation amount setting step.

6. A non-transitory computer readable medium storing a program causing a computer to execute a process for irradiating an object with a charged particle beam, the process comprising:

setting an irradiation amount of a charged-particle beam at a plurality of target scanning positions on a scanning line of the charged-particle beam with which a scanning member scans an object to be irradiated; and setting a target scanning speed of the charged-particle beam at each of the target scanning positions on the basis of the irradiation amount set by the irradiation amount setting.

* * * * *